United States Patent
Ekstedt

(10) Patent No.: US 9,821,940 B2
(45) Date of Patent: Nov. 21, 2017

(54) PACKAGING UNIT HAVING IMPROVED SEALING AND A METHOD OF FORMING A PACKAGING UNIT HAVING IMPROVED SEALING

(71) Applicant: SCA Hygiene Products AB, Göteborg (SE)

(72) Inventor: Sofia Ekstedt, Göteborg (SE)

(73) Assignee: SCA HYGIENE PRODUCTS AB, Gothenburg (SE)

(*) Notice: Subject to any disclaimer, the term of this patent is extended or adjusted under 35 U.S.C. 154(b) by 0 days.

(21) Appl. No.: 15/348,606

(22) Filed: Nov. 10, 2016

(65) Prior Publication Data

US 2017/0057719 A1    Mar. 2, 2017

Related U.S. Application Data

(62) Division of application No. 15/029,411, filed as application No. PCT/SE2013/051233 on Oct. 23, 2013, now Pat. No. 9,545,344.

(51) Int. Cl.
*A61B 17/06* (2006.01)
*B65D 75/20* (2006.01)
(Continued)

(52) U.S. Cl.
CPC ........ *B65D 75/20* (2013.01); *A61F 13/15739* (2013.01); *A61F 13/15747* (2013.01);
(Continued)

(58) Field of Classification Search
CPC ................ A61F 13/551; A61F 13/5514; A61F 13/5515; A61F 13/15747; B65D 65/14;
(Continued)

(56) References Cited

U.S. PATENT DOCUMENTS 3,217,871 A    11/1965    Lee
4,555,022 A    11/1985    Eagon et al.
(Continued)

FOREIGN PATENT DOCUMENTS

EP    0 471 385 A1    2/1992
EP    0 472 376 A1    2/1992
(Continued)

OTHER PUBLICATIONS

Written Opinion (PCT/IPEA/408) dated Oct. 2, 2015, by the Swedish Patent Office as the International Preliminary Examining Authority for International Application No. PCT/SE2013/051233.
(Continued)

*Primary Examiner* — Luan K Bui
(74) *Attorney, Agent, or Firm* — Buchanan Ingersoll & Rooney PC

(57) ABSTRACT

A packaging unit for hygiene articles is formed from a sheet of material having an inner surface and an outer surface. The inner surface includes an edge zone including an inner edge portion and an outer edge portion. The sheet has at least one folding axis dividing the sheet into a first region and a second region. The inner edge portion and the outer edge portion of the edge zone of the first region is provided with adhesive, and the other of the inner edge portion and the outer edge portion of the edge zone of the first region is adhesive-free. Further, one of the inner edge portion and the outer edge portion of the edge zone of the second region is provided with adhesive, and the other is adhesive-free in a complementary manner to the edge zone of the first region.

20 Claims, 8 Drawing Sheets

(51) Int. Cl.

| | | |
|---|---|---|
| *A61F 13/551* | (2006.01) | |
| *B65D 65/14* | (2006.01) | |
| *A61F 13/15* | (2006.01) | |
| *B32B 37/12* | (2006.01) | |
| *B32B 38/00* | (2006.01) | |
| *B31B 19/64* | (2006.01) | |
| *B31B 21/00* | (2006.01) | |
| *B65D 75/58* | (2006.01) | |

(52) U.S. Cl.
CPC ........ *A61F 13/551* (2013.01); *A61F 13/5514* (2013.01); *A61F 13/5515* (2013.01); *A61F 13/55135* (2013.01); *B31B 19/64* (2013.01); *B31B 21/00* (2013.01); *B32B 37/12* (2013.01); *B32B 38/0004* (2013.01); *B65D 65/14* (2013.01); *B65D 75/58* (2013.01); *B31B 2219/603* (2013.01); *B31B 2221/102* (2013.01); *B32B 2555/02* (2013.01); *B65D 2209/00* (2013.01); *B65D 2575/586* (2013.01)

(58) Field of Classification Search
CPC ..... B65D 75/20; B31B 2221/20; B31B 21/00; B31B 19/62; B65B 7/14
USPC .................. 206/438, 440, 441, 494; 53/455; 493/186, 243, 254, 264; 604/385.02, 604/385.05
See application file for complete search history.

(56) References Cited

U.S. PATENT DOCUMENTS

| | | | |
|---|---|---|---|
| 4,781,712 A | 11/1988 | Barabino et al. | |
| 4,917,675 A | 4/1990 | Taylor et al. | |
| 5,167,739 A * | 12/1992 | Hutchinson | B42D 15/08 156/291 |
| 5,375,764 A * | 12/1994 | Sauerwine | B65D 27/04 229/304 |
| H1454 H | 6/1995 | Cucuzza et al. | |
| H001454 H | 6/1995 | Ccuzza | |
| 5,569,230 A | 10/1996 | Fisher et al. | |
| 5,571,586 A | 11/1996 | Gobran | |
| 5,769,837 A | 6/1998 | Parr | |
| 5,829,670 A | 11/1998 | Lombardo | |
| 6,126,064 A * | 10/2000 | Hutchinson | B42D 15/08 229/313 |
| 6,135,506 A | 10/2000 | Chess | |
| 6,412,687 B1 * | 7/2002 | Steitz | B42D 15/08 229/305 |
| 6,500,293 B1 | 12/2002 | Dexter | |
| 7,004,320 B1 | 2/2006 | Schmidt et al. | |
| 7,810,641 B2 | 10/2010 | Hungler | |
| 8,460,260 B2 | 6/2013 | Fung | |
| 2010/0121299 A1 | 5/2010 | Cooper | |
| 2010/0298797 A1 * | 11/2010 | Ehlenbach | A61F 13/5515 604/385.02 |

FOREIGN PATENT DOCUMENTS

| | | |
|---|---|---|
| GB | 2 153 779 A | 8/1985 |
| JP | 2004-514539 A | 5/2004 |
| WO | WO 88/10219 A1 | 12/1988 |
| WO | WO 94/14396 A1 | 7/1994 |
| WO | WO 99/11683 A1 | 3/1999 |
| WO | WO 02/45640 A1 | 6/2002 |
| WO | 2013/162430 A1 | 10/2013 |

OTHER PUBLICATIONS

International Preliminary Report on Patentability (PCT/IPEA/409) dated Jan. 5, 2016, by the Swedish Patent Office as the International Preliminary Examining Authority for International Application No. PCT/SE2013/051233.
International Search Report and Written Opinion of the International Searching Authority (PCT/ISA/210, PCT/ISA/220 and PCT/ISA/237) dated Feb. 9, 2015, by the Swedish Patent Office as the International Searching Authority for International Application No. PCT/SE2014/051215.
Written Opinion (PCT/IPEA/408) dated Oct. 13, 2015, by the Swedish Patent Office as the International Preliminary Examining Authority for International Application No. PCT/SE2014/051215.
International Preliminary Report on Patentability (PCT/IPEA/409) dated Jan. 5, 2016, by the Swedish Patent Office as the International Preliminary Examining Authority for International Application No. PCT/SE2014/051215.
International Search Report (PCT/ISA/210) dated Jan. 15, 2013, by the Swedish Patent Office as the International Searching Authority for International Application No. PCT/SE2012/050425.
Written Opinion (PCT/ISA/237) dated Jan. 15, 2013, by the Swedish Patent Office as the International Searching Authority for International Application No. PCT/SE2012/050425.
Written Opinion (PCT/ISA/237) dated May 22, 2014, by the Swedish Patent Office as the International Searching Authority for International Application No. PCT/SE2012/050425.
International Preliminary Report on Patentability (PCT/IPEA/409) dated Jul. 22, 2014, by the Swedish Patent Office as the International Examining Authority for International Application No. PCT/SE2012/050425.
The extended European Search Report dated May 4, 2017, by the European Patent Office in corresponding European Patent Application No. 13894060.6-1308. (5 pages).
International Search Report and Written Opinion of the International Searching Authority (PCT/ISA/210, PCT/ISA/220 and PCT/ISA/237) dated Jun. 18, 2014, by the Swedish Patent Office as the International Searching Authority for International Application No. PCT/SE2013/051233.

* cited by examiner

PACKAGING UNIT HAVING IMPROVED SEALING AND A METHOD OF FORMING A PACKAGING UNIT HAVING IMPROVED SEALING

CROSS REFERENCE TO RELATED APPLICATION

This application is a divisional of U.S. patent application Ser. No. 15/029,411, filed Apr. 14, 2016, which is a National Stage of PCT/SE2013/051233, filed Oct. 23, 2013, the disclosures of all of which are incorporated herein by reference in their entirety.

TECHNICAL FIELD

The present invention relates to a packaging unit for hygiene articles, the unit being formed from a sheet of material, the sheet having an inner surface and an outer surface, the inner surface comprising an edge zone comprising an inner edge portion and an outer edge portion, the sheet having at least one folding axis, the folding axis dividing the sheet into a first region and a second region. The present invention also relates to a method of forming a packaging unit for hygiene articles from a sheet of material, a web of material for forming packaging units, as well as to a method of forming a web of material for forming packaging units.

BACKGROUND OF THE INVENTION

Disposable hygiene articles, such as sanitary napkins and panty liners, are normally packaged individually in e.g. an easy wrap or a single wrap. Individual packages facilitate hygienic carrying of single articles for future use, e.g. in a handbag. The edges of the individual packages are often sealed by means of ultrasonic welding or heat welding. Further, the packaging units are often used both as a means for packaging an unused article and for disposal of the used article.

It is desirable that used articles of this kind can be disposed of discretely and hygienically. This may be particularly important when the user lacks the possibility to dispose of the used article immediately after the used article has been replaced, e.g. when there is no waste bin available in the toilet area. In this case, the user may need to put the used article in e.g. the handbag or backpack, which requires that the package is tightly sealed in order to avoid staining and odour.

The disposal problem has been an object of quite an intensive investigation, and several solutions have been suggested.

GB 2 153 779 discloses a wrapper sheet that may be provided with a pouch formed by overlaying at least a portion of the wrapper with a sheet of liquid impermeable material which is affixed to the wrapper on three sides. The pouch is used to receive the soiled article. Such a wrapper suffers from disadvantages of requiring an additional amount of material, and not being able to form a tight disposal package.

Another common solution for disposing of used hygiene articles is disclosed in e.g. WO 94/14396. This document discloses a fold and wrap package comprising a wrapper comprising a single strip of material having a flap panel, a central panel and an end panel, and a tape tab for securing the wrapper in a disposal configuration. A major disadvantage of such a wrapper is that it is not possible to form a tightly sealed package when the article is to be disposed of.

WO 88/10219 discloses a packaging unit which is formed by folding an elongated sheet of material provided along the mutually parallel edges thereof with a continuous or broken narrow coating of pressure-sensitive adhesive by means of which the container part is held together, with adhesive surfaces lying against and bonding to adhesive surfaces. The packaging unit further comprises a lid coated at least partially with a pressure-sensitive adhesive so as to enable the lid to be refastened to the outside of the container part. Such a packaging unit thus has very strongly sealed side seams where the adhesive-coated surfaces are in contact with each other, and a resealable lid providing a tightly sealed disposal package. However, since the adhesive-coated surfaces are in contact with each other, it is impossible to unfold the sheet completely for positioning of a used item, which thus has to be inserted into the rather limited container part. This may be disadvantageous, since a used hygiene article often becomes more bulky than before use, making it difficult to insert it into the container part.

US H1454 discloses a reclosable sheet for packaging and disposal of hygiene articles. The sheet comprises edge adhesive strips positioned such that when the sheet is folded, the adhesive-coated areas do not come into contact with each other. In order to serve its purpose, the folding of the sheet has to be initiated from the adhesive-free transverse edge of the sheet. If the folding is initiated from the adhesive-coated transverse edge, two layers of adhesive will overlap each other, and the adhesive-free transverse edge will be positioned at the outer position of the package, i.e. the package will not be tightly sealed.

A conventional type of packaging unit intended for packaging single articles comprises an elongated rectangular sheet of material which is folded to form a bag-like package with a folded-over lid, also called e-folding. These known packaging units are welded along the edges by means of heat or ultrasound, and are opened by tearing along the welded seams at the edges, so that the package may be unfolded to expose the contents of the package.

The main drawback with welded packaging units of this kind is that they cannot be used satisfactorily as disposal bags since, once opened, the packages cannot be resealed and therefore do not allow a used article to be packaged in an acceptable manner with regard to hygiene. Furthermore, the unfolded packaging sheet has an inaesthetic appearance, since the broken welds are often uneven and frilly.

Hence there is a need for a packaging unit which can be used both for packaging a new hygiene article and for sanitary keeping and disposing of a used hygiene article, and which is aesthetically appealing.

SUMMARY OF THE INVENTION

The present invention provides a packaging unit which can be used both for packaging a new hygiene article and for safe and sanitary disposing of a used hygiene article. The packaging unit of the present invention provides a possibility of forming a tight package both for a new and a used article, thus keeping the new article sanitary and clean prior to use, and eliminating the risk of staining and odour when a used article is packaged. The packaging unit is easy to unfold and reseal, and is aesthetically appealing.

As used herein, the term "inner surface" refers to the surface of the packaging unit facing the product positioned inside the packaging unit, and the term "outer surface" refers to the surface opposite to the inner surface, i.e. the surface facing the ambient.

By the term "edge zone" is meant a portion of the packaging unit adjacent to the edges of the packaging unit. The width of an edge zone may be varied.

The term "inner edge portion" refers to the portion of the edge zone positioned towards the centreline of the packaging unit.

The term "outer edge portion" refers to the portion of the edge zone positioned towards the edge of the packaging unit.

By the term "single ply" is meant a packaging unit comprising a single ply of a coherent material. The examples of a single ply packaging unit may be a plastic film, such as a polyethylene film, a nonwoven material, a metallic foil or the like. A single ply material may be a non-homogenous material such as a plastic film material comprising integrated layers or a nonwoven material having varying fibre composition in different parts of the material. A single ply material as used herein does not comprise materials having separable layers.

By the term "laminate" is meant a packaging unit comprising at least two united separable plies of material that can be the same or different. In the context of the present invention, the laminate may for example be constituted of two separable plies of plastic film, a film and nonwoven, two plies of nonwoven, or the like.

By the term "transverse cutting zone" is meant an area of the web of material where an incision is made in order to separate a piece of the web of material, thus forming a sheet for forming a packaging unit of the present invention.

By the term "release agent" is meant a substance being able to adjust the adhesive strength of an adhesive bond between two adhered surfaces.

The present invention provides a packaging unit for hygiene articles and a method of forming a packaging unit, which substantially eliminate the drawbacks of the packaging units discussed above.

The packaging unit for hygiene articles according to the present invention is formed from a sheet of material having an inner surface and an outer surface, the inner surface comprising an edge zone comprising an inner edge portion and an outer edge portion. The sheet has at least one folding axis, the folding axis dividing the sheet into a first region and a second region. The packaging unit according to the present invention is characterized in that one of the inner edge portion and the outer edge portion of the edge zone of the first region is provided with adhesive, and the other of the inner edge portion and the outer edge portion of the edge zone of the first region is adhesive-free. Further, a characteristic feature of the present invention is that one of the inner edge portion and the outer edge portion of the edge zone of the second region is provided with adhesive, and the other of the inner edge portion and the outer edge portion of the edge zone of the second region is adhesive-free in a complementary manner to the edge zone of the first region. In other words, when the sheet is folded about the folding axis, the edge portion carrying adhesive in the first region is brought in contact with the adhesive-free edge portion in the second region, and the edge portion carrying adhesive in the second region is brought in contact with the adhesive-free edge portion in the first region. Further, at least a section of the adhesive-free edge portion in at least one of the first and second regions is provided with a release agent in order to be able to control the adhesive strength of the adhesive used in the present invention.

A suitable adhesive to be used with the packaging unit of the present invention is pressure-sensitive hotmelt adhesive having an unlimited open time, meaning that the adhesive can bond to another substrate at any time.

The pressure-sensitive adhesive used with the packaging unit is one which has a very high self-adhesion but which can be readily separated or released from other materials, such as plastic materials or paper which has been treated with a release agent. A major advantage of the packaging unit according to the present invention is that it can be completely unfolded when a new hygiene article is about to be taken out. In contrast thereto, prior art packages having adhesively sealed edges with adhesive-coated edge portions being in contact with each other have too high adhesive strength of the adhesively sealed edges, and any attempt to completely unfold the package would lead to deforming, tearing and breakage of the packaging unit, making it unusable for discrete and hygienic disposal of the used article. As the adhesive-coated edge portions of the packaging unit of the present invention are not in contact with each other when the packaging unit is folded, the packaging unit can be readily opened and resealed, providing a tight disposal package. At the same time, the tensile strength of the adhesively sealed edges of the packaging unit using the adhesive pattern of the present invention is sufficient to provide a tight package for both a new and a used article, and low enough to provide a readily-opened package.

Using a release agent permits the provision of a packaging unit comprising an adhesive having adequate strength to keep the packaging unit tightly sealed prior to opening, while the packaging unit may still be opened without using unduly high forces, potentially destroying the packaging unit and making it unsuitable for disposal purposes, and at the same time strength sufficient to form a tight packaging unit when the packaging unit is resealed.

The release agent may be provided on one of the adhesive-free edge portion. The release agent may also be provided on several of the adhesive-free edge portions, or on all of the adhesive-free edge portions of the absorbent article.

The release agent may form a coating covering the entire adhesive-free edge portion of the packaging unit. Also, the release agent may be applied in a pattern throughout the entire length of the adhesive-free edge portion. The pattern may be continuous, such as spiral, wave, zigzag, helix, or intermittent, such as lines, dots, crosses, stars, squares. Further, it is conceivable that the release agent is arranged on a section of the adhesive-free edge portion. The area of the section covered with a release agent may constitute 10-90% of the area of the corresponding adhesive-coated edge portion, preferably 30-70%, more preferably 40-60% of the area of the corresponding adhesive-coated edge portion.

The geometrical shape of the sheet can vary depending on the type of the hygiene article to be packaged. The sheet may be circular, triangular, square, rectangular, or any other shape suitable for the hygiene article to be packaged. It is desirable, however, that the sheet has at least one axis of symmetry.

As mentioned above, the packaging unit comprises at least one folding axis. The number of folding axes may vary depending on how the packaging unit is intended to be folded. It is preferred that the packaging unit comprises between one and three folding axes.

The prevailing shape of the sheet of material for forming a packaging unit is square or rectangular. Such a sheet according to the present invention has side edges, referred to herein as longitudinal edges, transverse edges and corner portions, the edge zones of the first and second regions of the sheet of material being arranged along the longitudinal edges. The edge portions covered with adhesive, the adhesive-free portions and the portions carrying a release agent are thus positioned along the longitudinal edges. In order to avoid that the edges of the sheet curl up or crinkle when the packaging unit is opened, the adhesive and/or the release agent provided on the outer edge portions may be positioned at a distance from the longitudinal edges. This distance may be between 0.5-5 mm, preferably between 1-3 mm. Also, this distance may be 0 mm, meaning that the adhesive and/or the release agent are provided such that they cover the entire outer edge portion all the way to the longitudinal edges.

The width of the adhesive-covered edge portions may be varied depending on the adhesive strength desired. The wider the adhesive-covered edge zones, the stronger the sealing. The width of the adhesive-covered edge portions may be same or different in the different regions.

The length of the adhesive-covered edge portions in each region may be equal to the length of each region, or may be 0.1-4 millimetres shorter than the length of each region.

Further, at least one of the transverse edges of the packaging unit according to the present invention is preferably provided with adhesive. In order to facilitate opening, at least one of the corner portions may be free from adhesive such that a gripping tab is formed.

As mentioned above, one of the most common folding patterns for individually wrapped hygiene products is so called e-folding. In this case the sheet has two folding axes, dividing the sheet into a first region, a second region and a third region. The packaging unit may then be formed, wherein the sheet is folded along the folding axes with the first, second and third regions in an overlapping configuration.

According to the present invention, when the sheet has two folding axes dividing the sheet into a first, a second and a third region, and the packaging unit is formed by e-folding, the edge portion of the edge zone of the third region being provided with adhesive corresponds to the edge portion of the edge zone of the first region being provided with adhesive, and is complementary to the edge portion of the edge zone of the second region being provided with adhesive. Thus, a chessboard pattern of adhesive is formed along each of the longitudinal edge zones. Also, at least a section of the adhesive-free portion in at least one of the regions of the packaging unit is provided with a release agent.

The sheet for forming a packaging unit may be a single ply sheet of any suitable material known to the person skilled in the art, such as polyethylene film or nonwoven. The sheet may also be a laminate comprising at least two distinct layers. Laminates suitable for packaging of hygiene articles are assumed to be known to the person skilled in the art, and are not in any way limiting for the present invention.

If desired, the sheet for forming a packaging unit according to the present invention may be opaque in order to disguise the contents of the packaging unit, which is particularly important if the used article wrapped into the packaging unit of the present invention cannot be disposed immediately after replacement. Further, the sheet may comprise print, which may be beneficial for attracting the user's attention and improving the user's mood.

The sheet of material forming a packaging unit according to the present invention may comprise an odour-inhibiting or odour-neutralising substance. Such a substance may be applied in any suitable manner known to the person skilled in the art, e.g. as coating, activatable microcapsules, impregnated patches or the like.

It is conceivable that the sheet for forming a packaging unit according to the present invention may be stretchable or expandable, which may be advantageous if the hygiene article is greatly deformed during use, and may thus be difficult to wrap without deforming the packaging unit.

The adhesive used in the present invention may be a pressure-sensitive hotmelt adhesive, such as Lunatack® D656 BD 19 available from H. B. Fuller.

The release agent useful in the present invention may be a silicone-based release agent, or low-adhesion backsize coating (known as LAB coatings), exemplified by, but not limited to, those disclosed in WO99/11683, U.S. Pat. No. 5,571,586 or U.S. Pat. No. 7,004,320. In general, the invention is carried out by coating paper or plastic film with a nonstick coating, sometimes termed a release coating, such as a silicone polymer coating or a polysiloxane. Polysiloxanes are particularly useful non-stick coatings, and both solvent-based and solvent-free polysiloxanes can be used. The polysiloxanes are cured either thermally or by radiation.

The packaging unit for hygiene articles according to the present invention is formed by a method comprising the steps of:

providing a sheet having an inner surface and an outer surface, the inner surface comprising an edge zone comprising an inner edge portion and an outer edge portion, the sheet having at least one folding axis, the folding axis dividing the sheet into a first region and a second region;

providing one of the inner edge portion and the outer edge portion of the edge zone of the first region with adhesive, such that the other of the inner edge portion and the outer edge portion of the edge zone of the first region is adhesive-free;

providing one of the inner edge portion and the outer edge portion of the edge zone of the second region with adhesive, such that the other of the inner edge portion and the outer edge portion of the edge zone of the second region is adhesive-free in a complementary manner to the edge zone of the first region;

providing at least a section of said adhesive-free edge portion in at least one of said first and said second regions with a release agent;

folding the sheet about the folding axis, such that the edge portions carrying adhesive in the first region are brought in contact with the adhesive-free edge portions in the second region, and the edge portions carrying adhesive in the second region are brought in contact with the adhesive-free edge portions at the first region.

It should be noted that when a packaging unit comprising at least two folding axes, i.e. at least three regions, is folded, the adhesive-covered edge portions of the first region are brought into contact with the adhesive-free portions of the second region, and the adhesive-covered portions of the second region are brought into contact with the adhesive-free portions of the first region. The subsequently folded third region is folded over the outer surface of the first region forming a lid, and the adhesive-covered edge portions of the third region are thus brought into contact with the adhesive-free outer surface of the first region. In this particular case, the folding order may be reversed, i.e. the adhesive-covered edge portions of the second region are brought in contact with the adhesive-free portions of the third region, and the adhesive-covered portions of the third region are brought in contact with the adhesive-free portions of the second region. The lid may be formed by folding the first region over the outer surface of the third region. The adhesive pattern according to the present invention thus has the advantage of giving the user the possibility to fold the packaging unit in any order, and still obtain a liquid- and odour-tight package, ensuring that the used article is disposed of in a discrete and hygienic manner. Further, when the packaging unit of the present invention is used for disposal, the user may choose to roll up the packaging unit instead of folding it.

The present invention also relates to a web of material for forming packaging units for hygiene articles, wherein the packaging units are formed by cutting the web into sheets of appropriate size. The web of material of the present invention has a longitudinal direction running along a longitudinal central axis and a transverse direction perpendicular to the longitudinal direction, and comprises a plurality of transverse cutting zones arranged along a respective central cutting axis running in the transverse direction of the web. The transverse cutting zones are positioned at a distance from each other in the longitudinal direction of the web. Each of said transverse cutting zones comprises a central portion and a first and a second peripheral portion arranged on either side of the central portion in the transverse direction. At least a section of each of the transverse cutting zones of the web is provided with a release agent.

When the web of material according to the present invention is intended to be used for manufacturing e-folding packaging units comprising two folding axes as described above, several options are available for arranging the release agent.

First of all, the section of the transverse cutting zone being provided with the release agent may be arranged in the central portion of the transverse cutting zone, or in one or both of the peripheral portions of the transverse cutting zone.

Further, the section of the transverse cutting zone provided with a release agent may be arranged along the entire extension of the transverse cutting zone in the transverse direction of the web. In this case, the section provided with a release agent in the central portion of the transverse cutting zone is displaced in the longitudinal direction of the web in relation to the sections provided with a release agent in the first and second peripheral portions of the transverse cutting zone. When a packaging unit manufactured from the web according to this embodiment is folded, the sections provided with a release agent will not overlap.

In cases when the web of material according to the present invention is intended to be used for manufacturing packaging units comprising one folding axis as described above, the section of the transverse cutting zone being provided with the release agent may be arranged along the entire extension of the transverse cutting zone in the transverse direction such that the section provided with a release agent comprises a first part and a second part. The first part of the section provided with a release agent is displaced in the longitudinal direction in relation to the second part of the section provided with a release agent. The displacement point is positioned at the intersection of the longitudinal central axis and the central cutting axis. When a packaging unit manufactured from the web according to this embodiment is folded, the sections provided with a release agent will not overlap.

Of course, the web of material may be provided with adhesive in at least a section of the transverse cutting zone being free from release agent. Thus, adhesive may be arranged in a complementary manner as mentioned earlier, i.e. the sections of transverse cutting zones not carrying the release agent may carry adhesive.

The web according to the present invention may be made of any material suitable for manufacturing packaging units, i.e. a plastic film, a nonwoven, a laminate, or any other material known to the person skilled in the art.

The dimensions of a web of material of the present invention may vary depending on the size of the packaging units to be manufactured. Most typically, the web of material is in the form of a roll having a length of several hundred meters in the longitudinal direction, and a width in the transverse direction of 10-50 cm, preferably 15-40 cm, more preferably 20-30 cm.

The dimensions of the transverse cutting zone may vary depending on the size of the packaging unit to be manufactured, and on the adhesive strength required. The transverse cutting zone may have a width in the longitudinal direction of the web of 0.5-5 cm, preferably 1-4 cm, more preferably 2-3 cm. The length of the transverse cutting zone in the transverse direction of the web equals the width of the web of material in the transverse direction of the web.

The present invention further relates to a manufacturing method for providing a web of material for forming packaging units for hygiene articles, comprising the steps of:
  a) providing a web of material having a longitudinal direction running along a longitudinal central axis and a transverse direction perpendicular to the longitudinal direction, the web running in machine direction (MD) such that the longitudinal direction of the web coincides with the MD, the web comprising a plurality of transverse cutting zones, each of the transverse cutting zones being arranged along a central cutting axis running in the transverse direction of the web, the transverse cutting zones being positioned at a distance from each other in the longitudinal direction of the web;
  b) providing a portion of each of the transverse cutting zones of the web with adhesive in the transverse direction of the web;
  c) providing at least a section of the remaining portion of each of the transverse cutting zones of the web with a release agent in the transverse direction of the web; and
  d) cutting the web through the transverse cutting zones along the central cutting axes.

Of course, steps b) and c) may take place in any order, i.e. the web of material may first be provided with a release agent, and then with the adhesive on the portions of the transverse cutting zones being free from the release agent.

BRIEF DESCRIPTION OF THE DRAWINGS

Embodiments of the invention will now be described by way of example only and with reference to the accompanying drawings, of which.

DETAILED DESCRIPTION OF PREFERRED EMBODIMENTS

Figure 1:
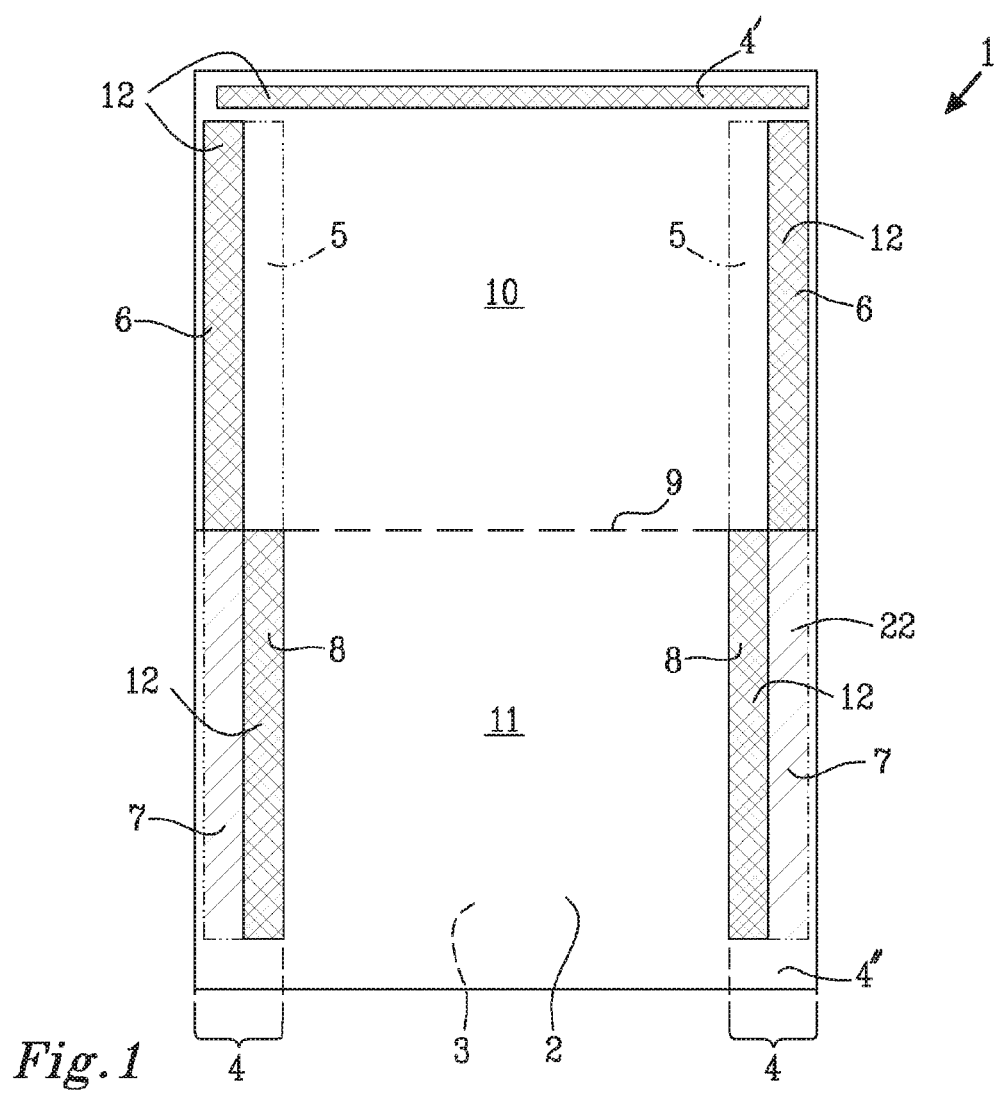
FIGS. 1-6 show various packaging units according to the present invention having one folding axis.
Figure 2:
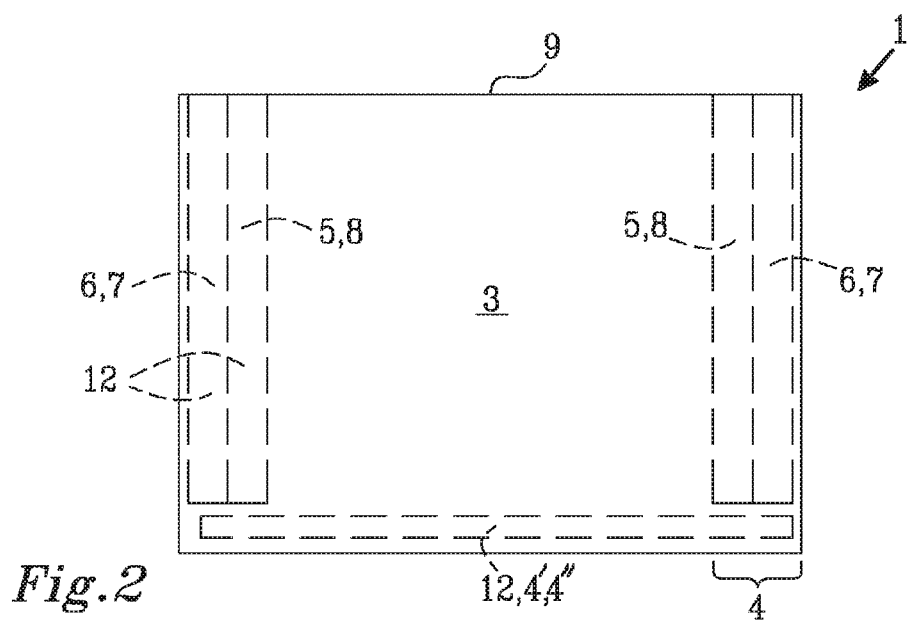

FIG. 1 depicts a packaging unit 1 for hygiene articles according to the present invention. The packaging unit is formed from a sheet of material having an inner surface 2 and an outer surface 3, the inner surface comprising an edge zone 4 comprising an inner edge portion 5, 8 and an outer edge portion 6, 7. The packaging unit 1 also comprises opposed transverse edge portions 4' and 4". The sheet has a folding axis 9, wherein the folding axis divides the sheet into a first region 10 and a second region 11. As shown in FIG. 1, the outer edge portion 6 of the edge zone 4 of the first region 10 is provided with adhesive 12, while the inner edge portion 5 of the edge zone 4 of the first region 10 is adhesive-free. Further, the inner edge portion 8 of the edge zone 4 of the second region 11 is provided with adhesive 12, while the outer edge portion 7 of the edge zone 4 of the second region 11 is provided with a release agent 22. Also, the transverse edge portion 4' of the first region 10 is provided with adhesive 12, while the transverse edge portion 4" of the second region 11 is adhesive-free. Thus, the adhesive pattern in the first region 10 is complementary to the adhesive pattern of the second region 11. This in turn means that, when the sheet is folded about the folding axis 9 as shown in FIG. 2, the edge portions 6 carrying adhesive in the first region 10 are brought in to contact with the edge portion 7 carrying the release agent 22 in the second region 11, the edge portions 8 carrying adhesive 12 in the second region 11 are brought in contact with the adhesive-free edge portions 5 in the first region 10, and the transverse edge portion 4' carrying adhesive 12 in the first region 10 is brought in contact with the adhesive-free transverse edge portion 4" in the second region 11. As can be seen from FIG. 2, the width of the sealing area corresponds to the sum of the widths of the adhesive portions 6, 8. Such a sealing ensures a tight package for both a new and a disposed article.

Figure 3:
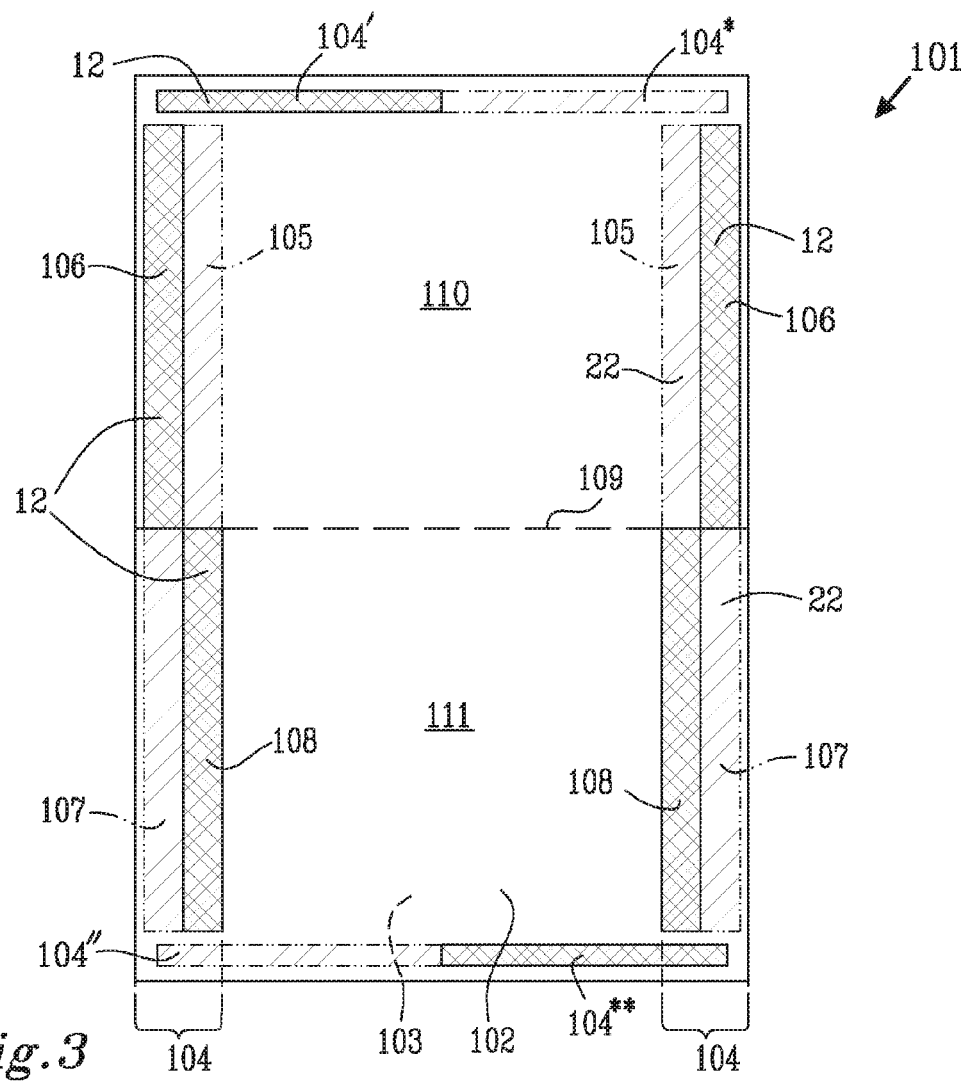
Figure 4:
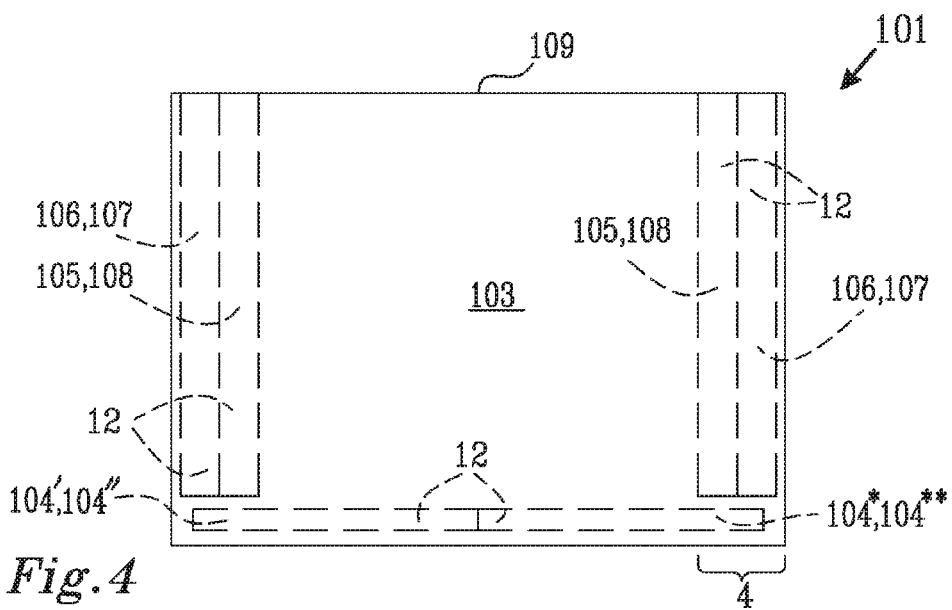

FIG. 3 depicts a packaging unit 101 for hygiene articles according to the present invention. The packaging unit is formed from a sheet of material having an inner surface 102 and an outer surface 103, the inner surface comprising an edge zone 104 comprising an inner edge portion 105, 108 and an outer edge portion 106, 107. The packaging unit 101 also comprises opposed transverse edge portions 104', 104* and 104", 104**. The sheet has a folding axis 109, wherein the folding axis divides the sheet into a first region 110 and a second region 111. As shown in FIG. 3, the outer edge portion 106 of the edge zone 104 of the first region 110 is provided with adhesive 12, while the inner edge portion 105 of the edge zone 104 of the first region 110 is provided with a release agent. Further, the inner edge portion 108 of the edge zone 104 of the second region 111 is provided with adhesive 12, while the outer edge portion 107 of the edge zone 104 of the second region 111 is provided with a release agent. Also, the transverse edge portion 104' of the first region 110 is provided with adhesive 12, while the transverse edge portion 104* of the first region 110 is provided with a release agent. Further, the transverse edge portion 104 of the second region 111 is provided with adhesive 12, while the transverse edge portion 104" of the second region 111 is provided with a release agent. Thus, the adhesive pattern in the first region 110 is complementary to the adhesive pattern of the second region 111. This in turn means that, when the sheet is folded about the folding axis 109 as shown in FIG. 4, the edge portions 106 carrying adhesive in the first region 110 are brought in contact with the edge portions 107 carrying the release agent 22 in the second region 111, the edge portions 108 carrying adhesive 12 in the second region 111 are brought in contact with the edge portions 105 carrying the release agent 22 in the first region 110, the transverse edge portion 104' carrying adhesive 12 in the first region 110 is brought in contact with the transverse edge portion 104" carrying the release agent 22 in the second region 111, and the transverse edge portion 104 carrying adhesive 12 in the second region 111 is brought in contact with the transverse edge portion 104* carrying the release agent in the first region 110. As can be seen from FIG. 4, the width of the sealing area along the longitudinal edges corresponds to the sum of the widths of the adhesive edge portions 106, 108, and the length of sealing area along the transverse edges corresponds to the sum of the lengths of the adhesive portions 104' and 104**. Such a sealing ensures a tight package for both a new and a disposed article.

It should be noted that in the embodiments shown in FIGS. 1-4 the release agent 22 is applied as an essentially continuous coating.

Figure 5:
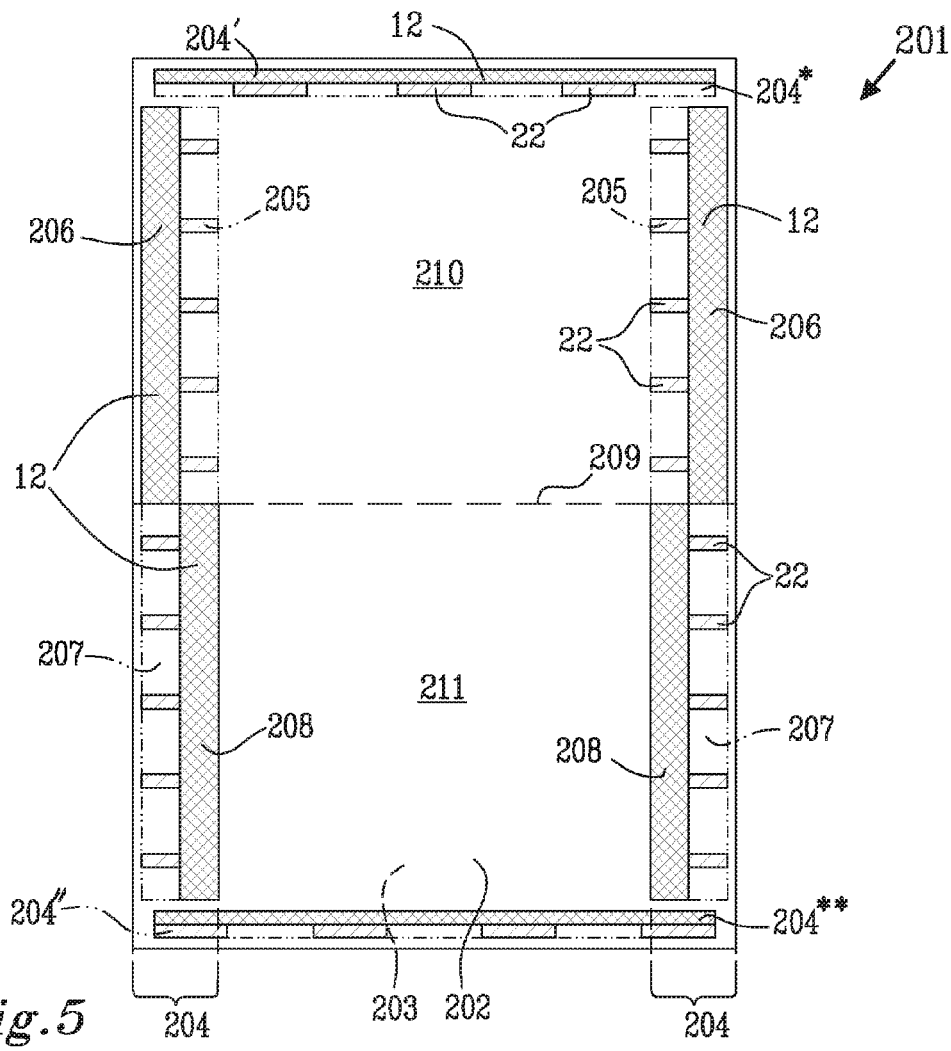
Figure 6:
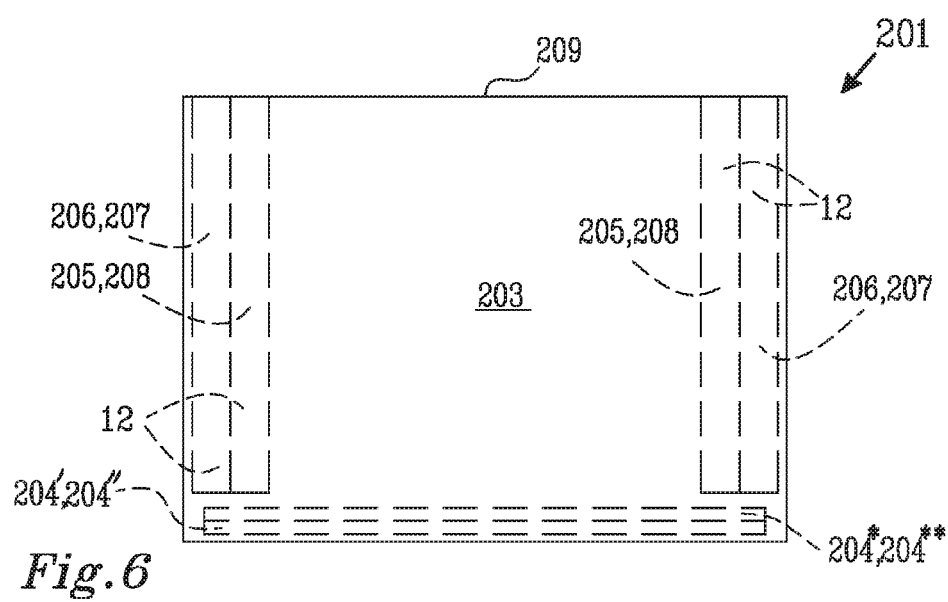

FIG. 5 illustrates a packaging unit 201 for hygiene articles according to the present invention. The packaging unit is formed from a sheet of material having an inner surface 202 and an outer surface 203, the inner surface comprising an edge zone 204 comprising an inner edge portion 205, 208 and an outer edge portion 206, 207. The packaging unit 201 also comprises a transverse edge portions 204', 204* and 204", 204**. The sheet has a folding axis 209, wherein the folding axis divides the sheet into a first region 210 and a second region 211. As shown in FIG. 3, the outer edge portion 206 of the edge zone 204 of the first region 210 is provided with adhesive 12, while the inner edge portion 205 of the edge zone 204 of the first region 210 is provided with a release agent 22 being applied in an intermittent pattern. Further, the inner edge portion 208 of the edge zone 204 of the second region 211 is provided with adhesive 12, while the outer edge portion 207 of the edge zone 204 of the second region 211 is provided with a release agent 22 being applied in an intermittent pattern. Also, the transverse edge portion 204' of the first region 210 is provided with adhesive 12, while the transverse edge portion 204* of the first region 210 is provided with a release agent 22 being applied in an intermittent pattern. Further, the transverse edge portion 204 of the second region 211 is provided with adhesive 12, while the transverse edge portion 204" of the second region 211 is provided with a release agent 22 being applied in an intermittent pattern. In the embodiment shown in FIG. 5, the intermittent pattern of the release agent 22 is in the form of lines. Thus, the adhesive pattern in the first region 210 is complementary to the adhesive pattern of the second region 211. This in turn means that, when the sheet is folded about the folding axis 209 as shown in FIG. 6, the edge portions 206 carrying adhesive in the first region 210 are brought in contact with the edge portions 207 provided with the release agent 22 in the second region 211, the edge portions 208 carrying adhesive 12 in the second region 211 are brought in contact with the edge portions 205 provided with the release agent 22 in the first region 210, the transverse edge portion 204' carrying adhesive 12 in the first region 210 is brought in contact with the transverse edge portion 204" provided with the release agent 22 in the second region 211, and the transverse edge portion 204 carrying adhesive 12 in the second region 211 is brought in contact with the transverse edge portion 204* provided with the release agent 22 in the first region 210. As can be seen from FIG. 6, the width of the sealing area along the longitudinal edges corresponds to the sum of the widths of the adhesive portions 206 and 208, and the width of the sealing area along the transverse edges corresponds to the sum of the widths of the adhesive portions 204' and **204\*\***. Such a sealing ensures a tight package for both a new and a disposed article.

It has been shown that applying the release agent 22 in an intermittent pattern, such as the one illustrated in FIGS. 5-6 is advantageous, since it is cost-efficient and provides an optimal adhesive strength, being weak enough to facilitate opening of the packaging unit containing an unused article, and strong enough to provide sufficient sealing of the packaging unit when a used article has been inserted into the packaging unit for disposal purposes.

Nevertheless, it is to be understood that in one and the same embodiment certain edge portions may be provided with an intermittent pattern of release agent, others may be provided with an essentially continuous coating and/or others may be provided with no release agent at all.

Figure 7:
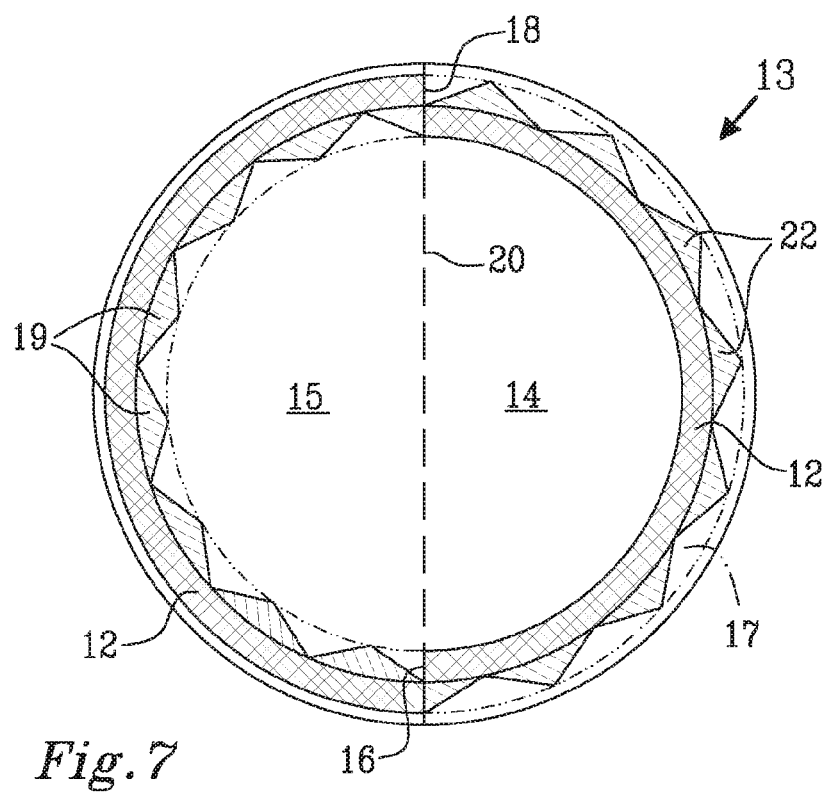
FIG. 7 shows a circular packaging unit according to the present invention.
Figure 8:
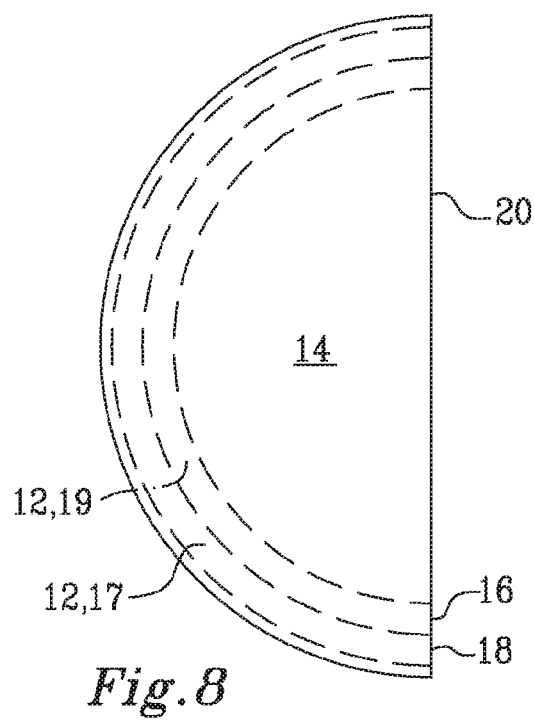
FIG. 8 shows the packaging unit depicted in FIG. 7 in a folded state.

FIG. 7 illustrates a packaging unit 13 having a circular shape. Such a packaging unit may be used for absorbent articles that are packaged by rolling rather than folding, such as tampons or breast pads. The packaging unit 13 has a folding axis 20 dividing the packaging unit 13 into a first region 14 and a second region 15. Each of the regions comprises an inner edge portion 16, 19 and an outer edge portion 17, 18. As shown in FIG. 7, the inner edge portion 16 of the first region 14 and the outer edge portion 18 of the second region 15 are provided with adhesive 12, while the outer edge portion 17 of the first region 14 and the inner edge portion 19 of the second region 15 are provided with a release agent 22 applied in a continuous zigzag pattern. Thus, the adhesive pattern in the first region 14 is complementary to the adhesive pattern of the second region 15. This in turn means that, when the sheet is folded about the folding axis 20 as shown in FIG. 8, the edge portions 16 carrying adhesive in the first region 14 are brought in contact with the edge portions 19 carrying the release agent 22 in the second region 15, and the edge portions 18 carrying adhesive 12 in the second region 15 are brought in contact with the edge portion 17 carrying the release agent 22 in the first region 14. As can be seen from FIG. 8, the width of the sealing area corresponds to the sum of the widths of the adhesive portions 16, 18.

Figure 9:
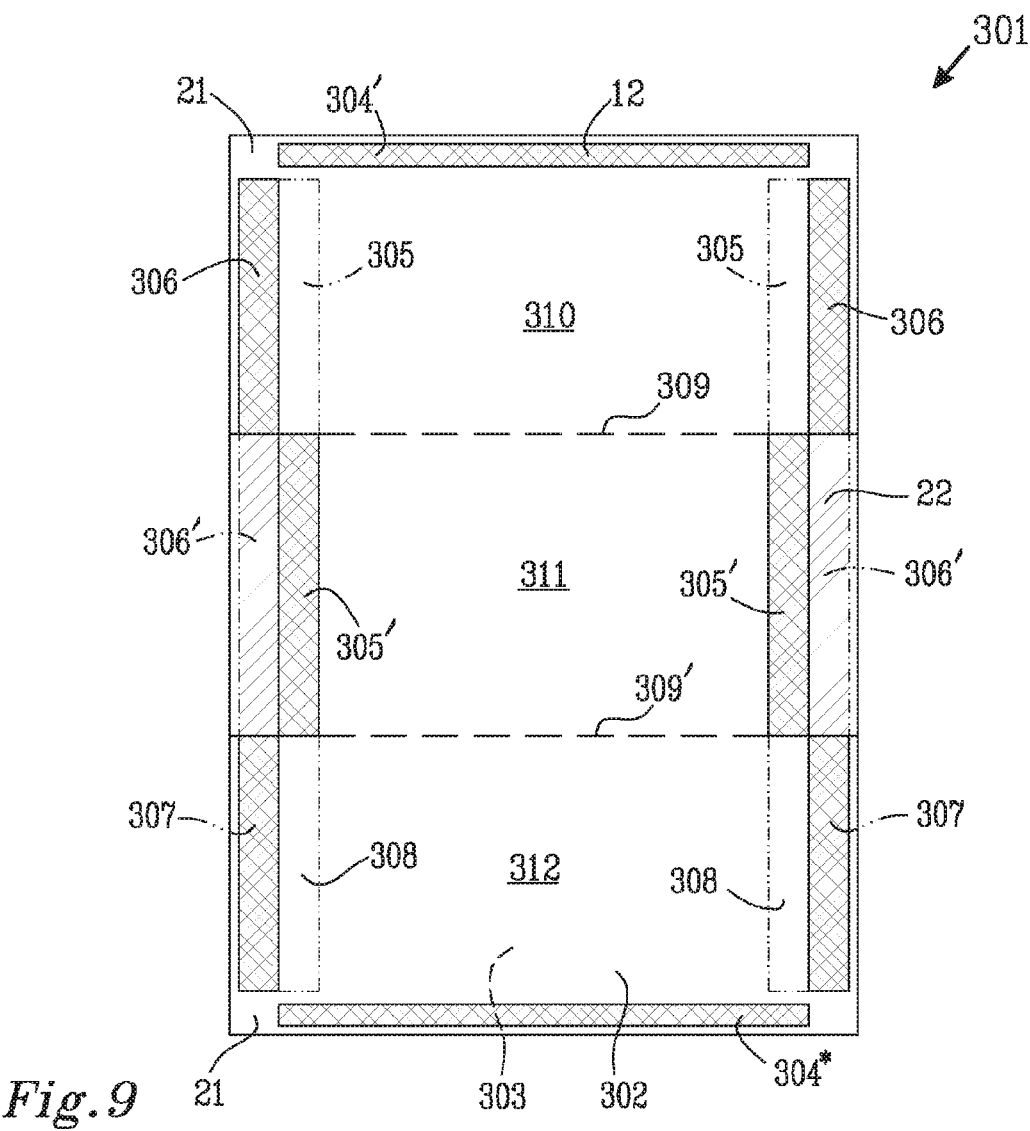
FIG. 9 shows a packaging unit according to the present invention having two folding axes.
Figure 10:
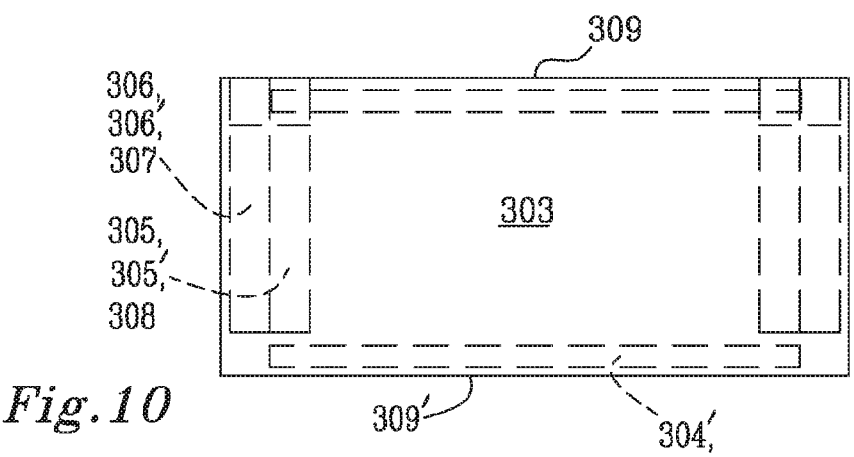
FIG. 10 shows the method of folding the packaging unit depicted in FIG. 9.

The most common packaging unit for individual packaging of absorbent articles is a rectangular sheet comprising two folding axes, longitudinal edges and transverse edges. Such an embodiment is illustrated in FIG. 9. The packaging unit 301 is a rectangular sheet comprising two folding axes 309, 309' dividing the packaging unit into a first region 310, a second region 311 and a third region 312. Each of the regions comprises an inner edge portion 305, 305', 308 and an outer edge portion 306, 306', 307. As shown in FIG. 9, the outer edge portions 306, 307 of the first and third regions respectively are provided with adhesive 12, while the inner edge portions 305, 308 of the first and third regions respectively are adhesive-free. The adhesive pattern of the second region 311 is complementary to the adhesive pattern of the first and third regions 310, 312, thus forming a chessboard pattern. In other words, the outer edge portion 306' of the second region 311 is adhesive-free and provided with a release agent 22, and the inner edge portion 305' of the second region 311 is provided with adhesive. This in turn means that, when the sheet is e-folded about the folding axes 309, 309' as shown in FIG. 10, the outer edge portions 306 of the first region 310 or the outer edge portions 307 of the third region 312 carrying adhesive 12 are brought in contact with the outer edge portions 306' carrying the release agent 22 in the second region 311, depending on which of the first and the third regions 310, 312 is brought in contact with the second region 311. Consequently, the inner edge portions 305' carrying adhesive 12 in the second region 311 are brought into contact with the adhesive-free inner edge portions 305 of the first region 310 or the adhesive-free inner edge portions 308 of the third region 312. As can be seen from FIG. 10, the width of the sealing area corresponds to the sum of the widths of the adhesive portions 306, 305'. It should be noted that the order in which the packaging unit is folded is irrelevant. For example, the packaging unit may be folded around the second folding axis 309', bringing the third region 312 in contact with the second region 311, sealing the outer edge portions 307, 306' and the inner edge portions 308, 305'. The packaging unit is subsequently folded around the first folding axis 309', bringing the first region 310 in contact with the outer surface of the third region 312, thus sealing the packaging unit (FIG. 10). The folding order may also be reversed. This is a great advantage, since when the packaging unit of the present invention is used for disposal, the user does not have to fold the packaging unit in any particular order to be able to obtain a tightly sealed package. The packaging unit will provide a tight and hygienic package regardless of the folding order.

It is of course conceivable to provide any one, two or three of the adhesive-free edge portions 305, 306' and 308 with a release agent.

In order to obtain a tight package, the transverse edges 304' and **304\*\* of the packaging unit 301 are provided with adhesive 12. When both transverse edges 304' and 304\*\*** are provided with adhesive, the folding order is irrelevant, as described above. It is also conceivable to provide only one of the transverse edges with adhesive. In this case, the folding must be initiated around the folding axis being positioned closest to the adhesive-free transverse edge, such that the region comprising the adhesive-covered transverse edge portion forms a lid and the adhesive positioned at the transverse edge portion seals the packaging unit.

In order to facilitate the opening of the package, the adhesive-covered portions are positioned such that at least one of the corner portions 21 of the packaging unit 301 is adhesive-free, thus forming a gripping tab that is gripped by the user upon opening the package. Moreover, the adhesive-free corner portion 21 serves as an evacuation opening when the packaging unit is sealed (FIG. 10).

Figure 11:
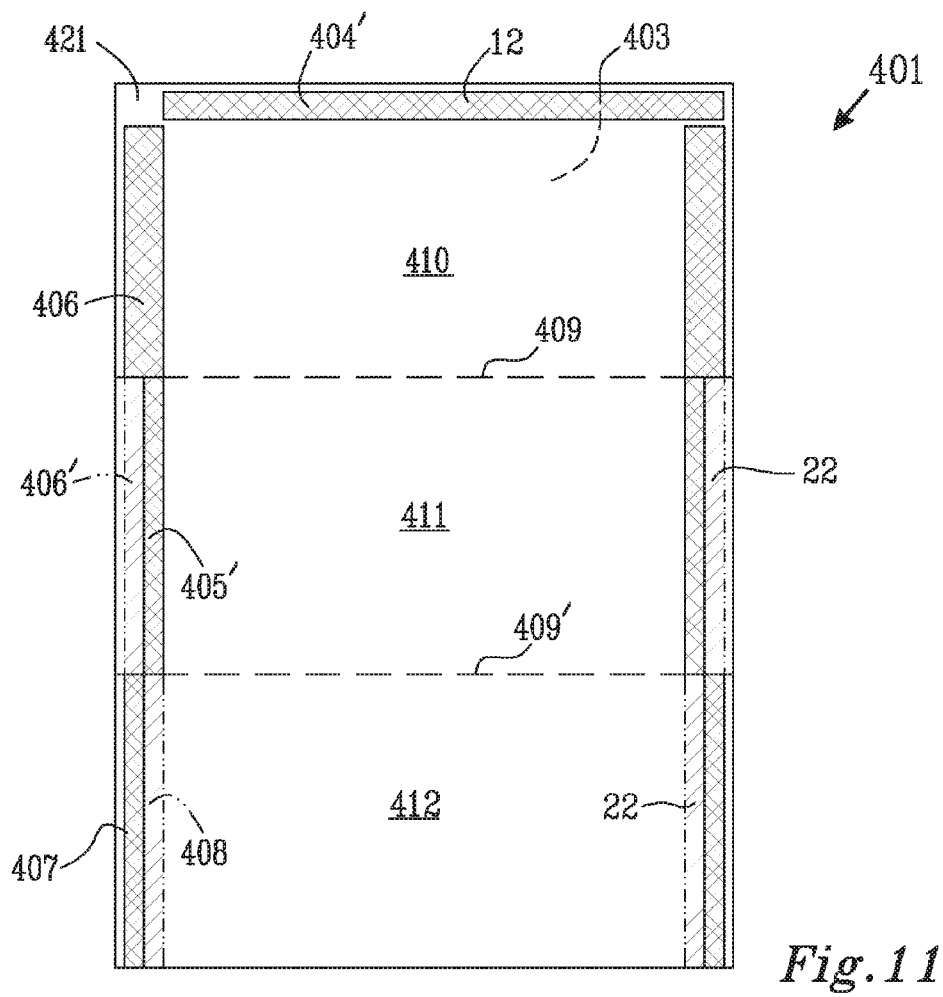
FIG. 11 shows a packaging unit according to the present invention having adhesive-covered portions of different widths.
Figure 12:
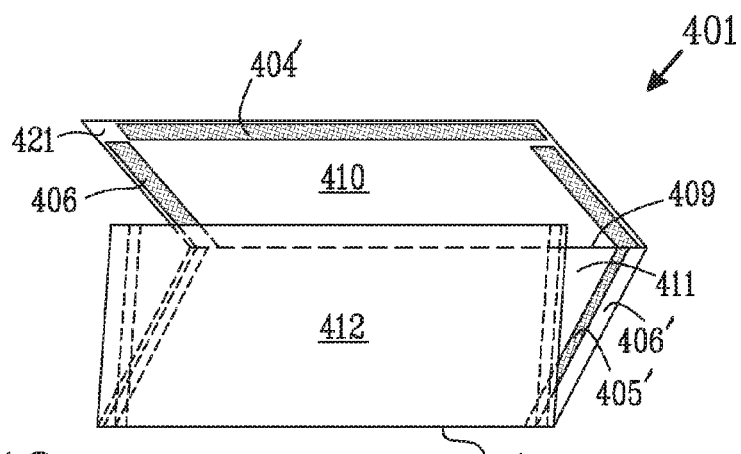
FIG. 12 shows the method of folding the packaging unit depicted in FIG. 11.

As has been explained above, the width of the sealing area is the sum of the widths of the adhesive-covered portions of the first and second region. It may be desirable to minimize the amount of adhesive and the width of the wrapping material for various reasons. This may be achieved if the width of the adhesive-covered portions in two of the adjacent regions is dimidiated in a way shown in FIG. 11. The packaging unit 401 has two folding axes 409, 409' dividing the packaging unit into a first region 410, a second region 411 and a third region 412. As can be seen from FIG. 11, the width of the adhesive-covered portions 405' and 407 of two of adjacent regions, in this case the second and the third region 411, 412, corresponds to half of the width of the adhesive-covered portion of the remaining region, in this case the first region 410, while the adhesive-free edge portions 406' and 408 carry a release agent. It is desirable that the adhesive-covered portion 405' of the second region 411 is complementary to the adhesive-covered portion 407 of the third region 412. If the adhesive pattern is as depicted in FIGS. 11 and 12, the folding has to be initiated around the folding axis positioned between the regions having dimidiated adhesive-covered portions if the packaging unit is intended to be re-opened, i.e. when an unused article is packed. Otherwise, the adhesive-covered portion 406 of the first region 410 would come in contact with the adhesive-covered portion 405' of the second region 411, thus ruling out the possibility of re-opening the packaging unit.

It should be noted that when the packaging unit according to the present invention is used for disposal, the user can choose to roll up the packaging unit and the soiled article positioned on it rather than folding it.

Figure 13:
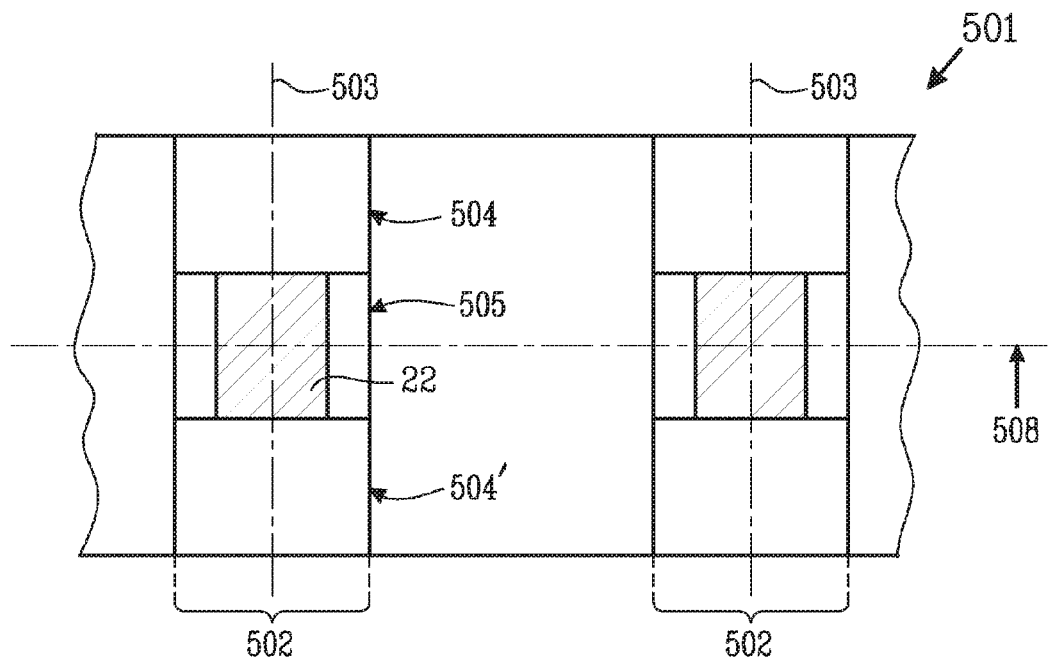
FIG. 13-15 depict a web of material for manufacturing packaging units according to the present invention.

FIG. 13 depicts a web of material 501 suitable for manufacturing packaging units according to the present invention. The web of material has a longitudinal direction running along a longitudinal central axis 508 and a transverse direction perpendicular to the longitudinal direction. The web 501 comprises a plurality of transverse cutting zones 502, each being arranged along a respective central cutting axis 503 running in the transverse direction of the web. The transverse cutting zones 502 are positioned at a distance from each other in the longitudinal direction of the web 501. Each of the transverse cutting zones comprises a central portion 505 and a first and a second peripheral portion 504, 504' arranged on either side of the central portion 505 in the transverse direction of the web. As shown in FIG. 13, the central portion 505 of the transverse cutting zone 502 is provided with a release agent 22.

Figure 14:
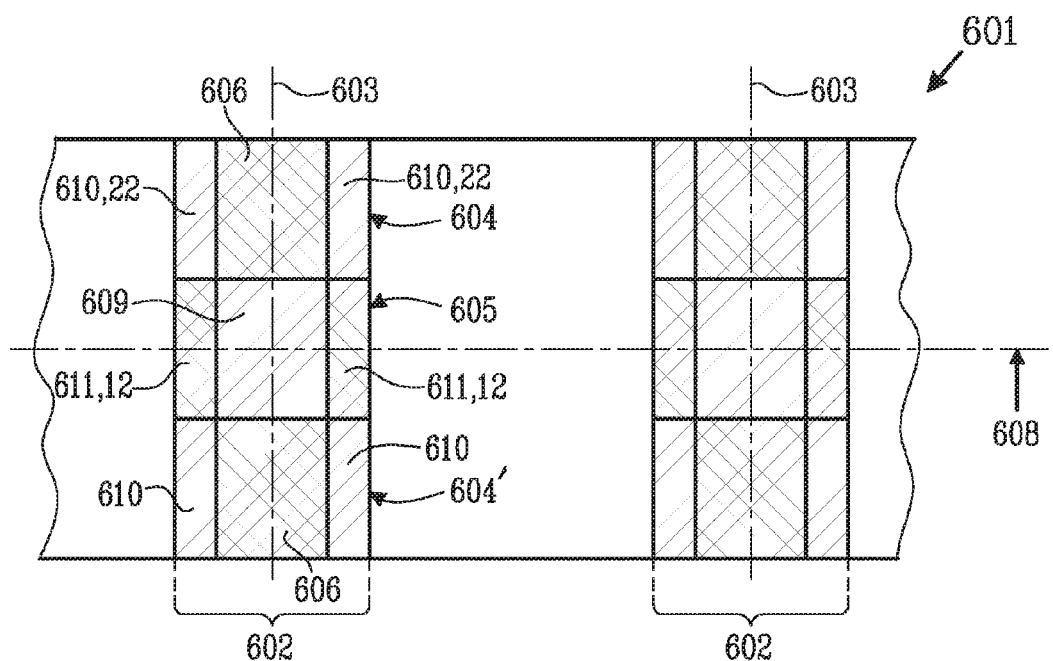

FIG. 14 illustrates a web of material 601, comprising a longitudinal central axis 608 and a plurality of transverse cutting zones 602, each being arranged along a respective central cutting axis 603 running in the transverse direction of the web. The transverse cutting zones 602 are positioned at a distance from each other in the longitudinal direction of the web 601. Each of the transverse cutting zones comprises a central portion 605 and a first and a second peripheral portion 604, 604' arranged on either side of the central portion 605 in the transverse direction of the web. As shown in FIG. 14, the release agent 22 is arranged along the entire length of the transverse cutting zone 602, such that the section 609 provided with a release agent 22 in the central portion 605 of the transverse cutting zone 602 is displaced in the longitudinal direction in relation to the sections 610, 610' provided with a release agent 22 in the first and second peripheral portions 604, 604' of the transverse cutting zone 602.

Further, the web 601 is provided with adhesive in sections of the transverse cutting zone 602 being free from release agent, such that a chessboard pattern of adhesive is formed in a manner described above. Thus, section 611 of the central portion 605 of the transverse cutting zone 602, as well as sections 606 and 606' of the first and the second peripheral portions 604, 604' of the transverse cutting zone 602 are provided with adhesive. When the web of material 601 is cut along the central cutting axes 603, packaging units similar to the ones depicted in FIG. 9 are formed.

Figure 15:
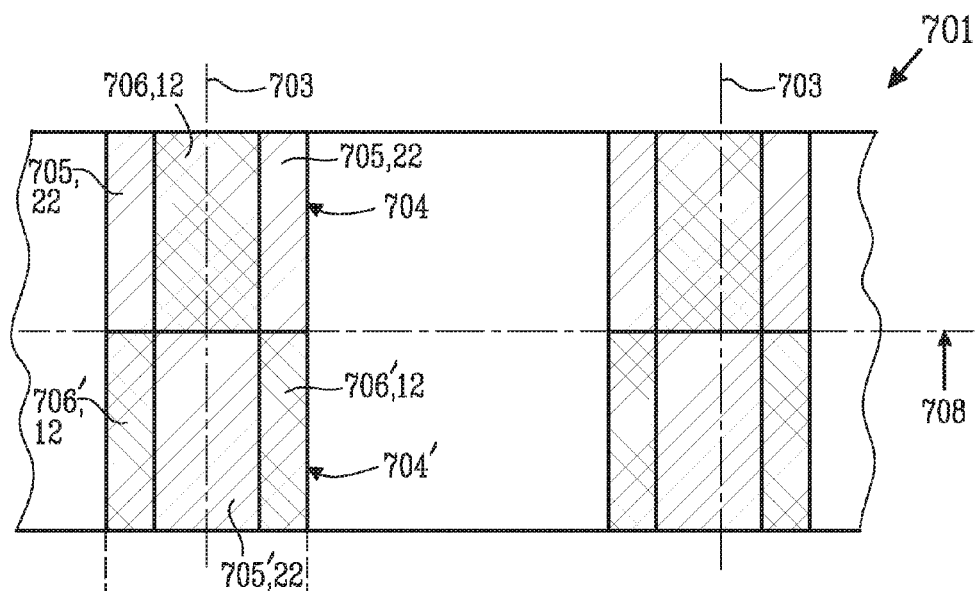

As mentioned previously, the packaging unit according to the present invention may comprise only one folding axis. In this case, the pattern of the adhesive and the release agent 22 on the web of material 701 of the present invention may be as the one depicted in FIG. 15. The section of the transverse cutting zone 702 being provided with the release agent 22 is arranged along the entire length of the transverse cutting zone 702. The section of the transverse cutting zone 602 provided with a release agent 22 comprises a first part 705 and a second part 705', wherein the first part 705 of the section provided with a release agent 22 is displaced in the longitudinal direction in relation to the second part 705' of the section provided with a release agent, wherein the displacement point is positioned at the intersection of the longitudinal central axis 708 and the central cutting axis 703.

Further, the web 701 is provided with adhesive in sections of the transverse cutting zone 702 being free from release agent. Thus, sections 706 and 706' of the transverse cutting zone 702 are provided with adhesive. When the web of material 701 is cut along the central cutting axes 703, packaging units similar to the ones depicted in FIG. 3 are formed.

Figure 16:
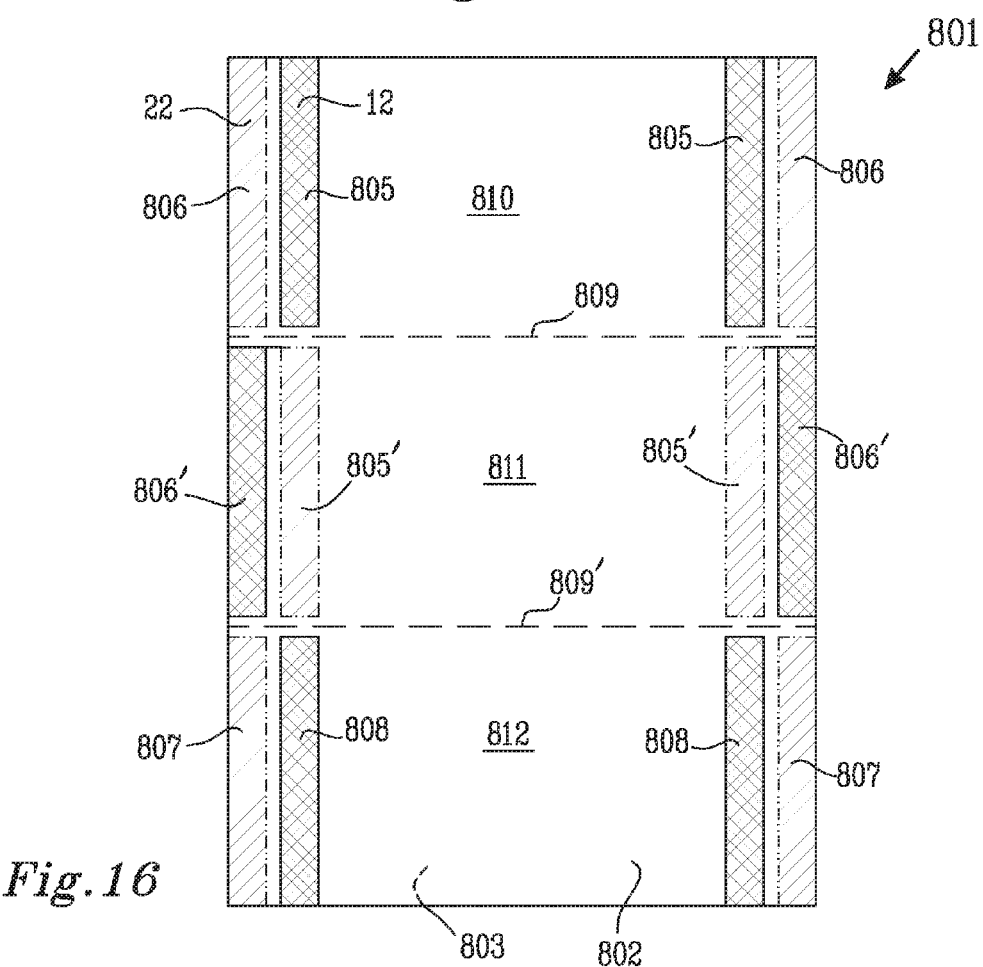
FIG. 16 shows a packaging unit according to the present invention having adhesive-carrying portions and portions provided with a release agent positioned at a distance from each other.

FIG. 16 depicts a packaging unit 801 comprising two folding axes 809, 809' dividing the packaging unit into a first region 810, a second region 811 and a third region 812. Each of the regions comprises an inner edge portion 805, 805', 808, respectively, and an outer edge portion 806, 806', 807, respectively. As shown in FIG. 16, the inner edge portions 805, 808 of the first and third regions respectively are provided with adhesive 12, while the outer edge portions 806, 807 of the first and third regions respectively are provided with a release agent 22 in the form of a uniform coating extending all the way to the longitudinal edges of the packaging unit 801. The adhesive pattern of the second region 811 is complementary to the adhesive pattern of the first and third regions 810, 812, thus forming a chessboard pattern. In other words, the outer edge portion 806' of the second region 811 is provided with adhesive extending all the way to the longitudinal edges of the packaging unit 801, while the inner edge portion 805' of the second region 811 is provided with a release agent 22. It should be noted that in the embodiment illustrated in FIG. 16, the treated sections of the outer edge portions 806, 806', 807, i.e. the sections being provided with either adhesive 12 or release agent 22, are arranged at a distance from the treated sections of the inner edge portions 805, 805', 808. Also, the treated sections of the edge portions in each region are arranged at a distance from the treated sections of the edge portions of the adjacent region.

Although the present invention has been described with reference to various embodiments, those skilled in the art will recognise that changes may be made without departing from the scope of the invention. It is intended that the detailed description be regarded as illustrative and that the appended claims including all the equivalents are intended to define the scope of the invention.

The invention claimed is:

1. A packaging unit for hygiene articles, the unit being formed from a sheet of material, said sheet having an inner surface and an outer surface, said inner surface comprising an edge zone comprising an inner edge portion and an outer edge portion, said sheet having at least one folding axis, said folding axis dividing said sheet into a first region and a second region, wherein one of said inner edge portion and said outer edge portion of said edge zone of said first region is provided with a resealable pressure-sensitive adhesive, and the other of said inner edge portion and said outer edge portion of said edge zone of said first region is adhesive-free;

one of said inner edge portion and said outer edge portion of said edge zone of said second region is provided with resealable pressure-sensitive adhesive, and the other of said inner edge portion and said outer edge portion of said edge zone of said second region is adhesive-free in a complementary manner to said edge zone of said first region, such that when said sheet is folded about said folding axis, said edge portion carrying resealable pressure-sensitive adhesive in said first region is brought in contact with said adhesive-free edge portion in said second region, and said edge portion carrying resealable pressure-sensitive adhesive in said second region is brought in contact with said adhesive-free edge portion in said first region, and in that at least a section of said adhesive-free edge portion in at least one of said first and said second regions is provided with a release agent.

2. The packaging unit according to claim 1, wherein said section of said adhesive-free edge portion provided with the release agent constitutes 10-90% of the area of said complementary edge portion carrying resealable pressure-sensitive adhesive.

3. The packaging unit according to claim 1, wherein the release agent is provided along the entire length of said adhesive-free edge portion.

4. The packaging unit according to claim 1, wherein the release agent is applied in a continuous pattern or as a coating.

5. The packaging unit according to claim 1, wherein the release agent is applied in an intermittent pattern.

6. The packaging unit according to claim 1, wherein the release agent is a silicone polymer or a polysiloxane.

7. The packaging unit according to claim 1, wherein said sheet of material is of substantially rectangular shape and comprises longitudinal edges, transverse edges and corner portions, said edge zones of said first and second regions of said sheet of material being arranged along said longitudinal edges.

8. The packaging unit according to claim 1, wherein said sheet of material comprises transverse edge zones and wherein at least a portion of one of said transverse edge zones is provided with resealable pressure-sensitive adhesive.

9. The packaging unit according to claim 8, wherein a portion of said transverse edge zone of said first region is provided with resealable pressure-sensitive adhesive, while the remaining portion of said transverse edge zone of said first region is adhesive-free, and a portion of said transverse edge zone of said second region is provided with resealable pressure-sensitive adhesive, while the remaining portion of said transverse edge zone of said second region is adhesive-free in a complementary manner to said transverse edge zone of said first region such that when said sheet is folded about said folding axis, said transverse edge portion carrying resealable pressure-sensitive adhesive in said first region is brought in contact with said adhesive-free transverse edge portion in said second region, and said transverse edge portion carrying resealable pressure-sensitive adhesive in said second region is brought in contact with said adhesive-free transverse edge portions in said first region, and wherein at least a section of said adhesive-free transverse edge portion in at least one of said first and said second regions is provided with a release agent.

10. The packaging unit according to claim 7, wherein at least one of said corner portions is free from adhesive such that a gripping tab is formed.

11. The packaging unit according to claim 7, wherein said sheet has two folding axes, dividing said sheet into a first region, a second region and a third region.

12. The packaging unit according to claim 11, wherein said sheet is folded along said folding axes with said first, second and third regions in an overlapping configuration.

13. The packaging unit according to claim 11, wherein the edge portion of said edge zone of said third region being provided with resealable pressure-sensitive adhesive corresponds to the edge portion of said edge zone of said first region being provided with resealable pressure-sensitive adhesive, and is complementary to the edge portion of said edge zone of said second region being provided with resealable pressure-sensitive adhesive, such that a chessboard pattern of resealable pressure-sensitive adhesive is formed along each of said longitudinal edges.

14. The packaging unit according to claim 13, wherein the width of the adhesive-covered edge portions of two adjacent regions is dimidiated compared to the width of the adhesive-covered portion of the remaining region.

15. The packaging unit according to claim 11, wherein at least a portion of one of said transverse edge zones is provided with resealable pressure-sensitive adhesive.

16. The packaging unit according to claim 1, wherein said sheet is opaque and/or comprises print.

17. The packaging unit according to claim 1, wherein said resealable pressure-sensitive adhesive is a pressure-sensitive hotmelt adhesive with unlimited open time.

18. The packaging unit according to claim 1, wherein said packaging unit is reclosable.

19. A method of forming a packaging unit for hygiene articles from a sheet of material, comprising the steps of:
  providing a sheet having an inner surface and an outer surface, said inner surface comprising an edge zone comprising an inner edge portion and an outer edge portion, said sheet having at least one folding axis, said folding axis dividing said sheet into a first region and a second region;
  providing one of said inner edge portion and said outer edge portion of said edge zone of said first region with resealable pressure-sensitive adhesive, such that the other of said inner edge portion and said outer edge portion of said edge zone of said first region is adhesive-free;
  providing one of said inner edge portion and said outer edge portion of said edge zone of said second region with resealable pressure-sensitive adhesive, such that the other of said inner edge portion and said outer edge portion of said edge zone of said second region is adhesive-free in a complementary manner to said edge zone of said first region;
  providing at least a section of said adhesive-free edge portion in at least one of said first and said second regions with a release agent;
  folding the sheet about said folding axis, such that the edge portion carrying resealable pressure-sensitive adhesive in said first region is brought in contact with the adhesive-free edge portion in said second region, and the edge portion carrying resealable pressure-sensitive adhesive in said second region is brought in contact with the adhesive-free edge portion at said first region.

20. The method according to claim 19, wherein said sheet has two folding axes dividing said sheet into a first region, a second region and a third region, the method further comprising the steps of:
  providing a portion of said edge zone of said third region with resealable pressure-sensitive adhesive;
  folding the sheet such that the inner surface of said third region is brought in contact with the outer surface of said first region.

* * * * *